United States Patent [19]
Decain et al.

[11] Patent Number: 5,834,642
[45] Date of Patent: Nov. 10, 1998

[54] DOWNSTREAM MONITOR FOR CMP BRUSH CLEANERS

[75] Inventors: Donald M. Decain, New York, N.Y.; Cuc K. Huynh, Jericho, Vt.; Robert A. Jurjevic, Glen Allen, Va.; Douglas P. Nadeau, Underhill, Vt.; Marc A. Taubenblatt, Pleasentville, N.Y.

[73] Assignee: International Business Machines Corporation, Armonk, N.Y.

[21] Appl. No.: 898,847

[22] Filed: Jul. 25, 1997

[51] Int. Cl.⁶ .......................... B05C 11/00; G01N 15/02; B03D 3/00
[52] U.S. Cl. ...................... 73/67.71; 73/19.12; 73/61.59; 422/683.1; 340/627
[58] Field of Search ................................. 73/61.71, 61.59, 73/961.72, 19.12, 863.52; 422/68.1

[56] References Cited

U.S. PATENT DOCUMENTS

| | | | |
|---|---|---|---|
| 3,203,253 | 8/1965 | Scheid | 73/432 |
| 3,373,352 | 3/1968 | Huigens | 324/41 |
| 3,514,996 | 6/1970 | Coustau | 73/153 |
| 3,715,913 | 2/1973 | Anderson | 73/61 R |
| 3,844,413 | 10/1974 | Mizushima | 209/209 |
| 3,952,580 | 4/1976 | Bennett | 73/61.4 |
| 4,336,136 | 6/1982 | Giguère | 210/178 |
| 5,257,087 | 10/1993 | Furuya | 356/336 |
| 5,439,551 | 8/1995 | Meikle et al. | 156/626.1 |
| 5,450,744 | 9/1995 | Martyn | 73/61.71 |
| 5,468,396 | 11/1995 | Allen et al. | 210/787 |
| 5,483,568 | 1/1996 | Yano et al. | 378/44 |
| 5,506,501 | 4/1996 | Fogel et al. | 324/204 |
| 5,509,375 | 4/1996 | Sayka et al. | 118/712 |
| 5,561,520 | 10/1996 | Williams | 356/335 |

*Primary Examiner*—Hezron E. Williams
*Assistant Examiner*—J. David Wiggins
*Attorney, Agent, or Firm*—DeLio & Peterson, LLC; Peter W. Peterson; Howard J. Walter, Jr.

[57] ABSTRACT

The present invention is a contamination measuring device and method of using the same according to a Chemical Mechanical Polishing (CMP) brush cleaner equipment/technology. A collection device is mounted in a brush cleaning device for collecting effluent which flows off of a wafer. The effluent is passed to a particle counter which measures the contamination levels of the effluent. A computer stores the data collected by the particle counter and computes the particles per liter of effluent and provides real time data. The contamination of the effluent corresponds to the contamination of the brushes in the cleaning device and therefore is means for predicting when the brushes in the cleaning device should be replaced.

7 Claims, 7 Drawing Sheets

FIG. 6a

DOWNSTREAM MONITOR FOR CMP BRUSH CLEANERS

BACKGROUND OF THE INVENTION

1. Field of the Invention

The present invention relates to Chemical Mechanical Polishing (CMP) wafer cleaning and, in particular, an apparatus for measuring effluent contamination in order to predict contamination of brushes in a brush cleaning device.

2. Problem to be Solved

The current approach in post Chemical Mechanical Polishing (CMP), utilizing brush cleaning to clean the polished substrates or wafers, is not adequately controlled. Consumable brushes, or sponges, are loaded with abrasive particles which re-contaminate the wafers being cleaned.

Experience with post CMP cleaning has shown that mechanical brush cleaning is very costly due to the high cost of the consumable brushes. The present technique uses replacement of brushes after an arbitrarily set number of wafers have been cleaned.

In brush clean processes, CMP slurry loading of the brush can be problematic. Slurry loading occurs when particles accumulate in brush bristles which can result in contamination of wafers during the cleaning process.

Bearing in mind the problems and deficiencies of the prior art, it is therefore an object of the present invention to provide an apparatus for measuring effluent contamination in a brush cleaning device whereby brush contamination can be predicted.

It is another object of the present invention to provide a device for reducing the expense of frequent brush replacements in a brush cleaning device.

A further object of the invention is to provide a device for measuring real time contamination in a brush cleaning device.

It is is yet another object of the present invention to provide a device for collecting effluent in a brush cleaning device, which effluent is a dependable vehicle for predicting contamination in the system.

Still other objects and advantages of the invention will in part be obvious and will in part be apparent from the specification.

SUMMARY OF THE INVENTION

The above and other objects and advantages, which will be apparent to one of skill in the art, are achieved in the present invention which is directed to, in a first aspect, a contamination measuring apparatus for measuring effluent contamination and predicting contamination in a wafer cleaning device comprising: a means for collecting effluent flowing from an area of an article being cleaned and passing the effluent into a narrower area, said means positioned adjacent to the article being cleaned, a means for holding a volume of effluent collected by said collecting means, said holding means positioned adjacent to said collecting means; and a particle counter connected to said holding means for measuring contamination of the effluent.

In another aspect the present invention relates to a contamination measuring apparatus for measuring effluent contamination in a cleaning device for cleaning wafers comprising: a reservoir; an effluent collector having a first opening for receiving effluent flowing off of an area of the wafer which is adjacent to the effluent collector, said collector having a second opening smaller than said first opening for discharging effluent into said reservoir, said reservoir for holding a volume of effluent collected by said effluent collector, said reservoir positioned adjacent to said effluent collector second opening; and a particle counter connected to said reservoir for measuring contamination of the effluent.

In another aspect, the present invention relates to method of measuring brush contamination in a cleaning device for cleaning wafers comprising the steps of: (a) collecting effluent flowing off an area of the wafer; (b) measuring the contamination of the effluent; (c) recording the contamination data in an electronic recording means; (d) comparing the recorded data to predetermined values recorded in said electronic recording means; and (e) taking an action, wherein said action is selected from the group consisting of reconditioning the brushes, replacing the brushes, rerunning the wafers, running a test wafer to diagnose corrective action, and adjusting the brush cleaning device.

In another aspect, the present invention relates to a method of measuring effluent contamination and predicting contamination in a wafer cleaning device comprising the steps of: (a) providing contamination measuring apparatus further comprising: (i) a means for collecting effluent flowing from an area of an article being cleaned and passing the effluent into a narrower area, said means positioned adjacent to the article being cleaned; (ii) a means for holding a volume of effluent collected by said collecting means, said holding means positioned adjacent to said collecting means; and (iii) a particle counter connected to said holding means for measuring contamination of the effluent; (b) passing the effluent from said holding means to said particle counter for measurement of contamination of the effluent; (c) recording the data collected by said particle counter in an electronic recordation means; (d) comparing the data collected by said particle counter to predetermined values stored in said electronic recordation means; and (e) taking an action, wherein said action is selected from the group consisting of reconditioning the brushes, replacing the brushes, rerunning the wafers, running a test wafer to diagnose corrective action, and adjusting the brush cleaning device.

In another aspect, the present invention relates to a method of measuring brush contamination in a cleaning device for cleaning wafers comprising the steps of: (a) providing a contamination measurement apparatus further comprising (i) a reservoir; (ii) an effluent collector having a first opening for receiving effluent flowing off of an area of the wafer which is adjacent to the effluent collector, said collector having a second opening smaller than said first opening for discharging effluent into said reservoir, said reservoir for holding a volume of effluent collected by said effluent collector, said reservoir positioned adjacent to said effluent collector second opening; and (iii) a particle counter connected to said reservoir for measuring contamination of the effluent; (b) passing the effluent from said effluent collector to said particle counter for measurement of contamination of the effluent; (c) recording the data collected by said particle counter in an electronic recordation means; (d) comparing the data collected by said particle counter to predetermined values stored in said electronic recordation means; (e) stopping said brush cleaning device when the data correlates to the predetermined values which indicate the cleanliness of brushes in said brush cleaning device; and (f) providing a trickle flow of liquid to said effluent collector while said brush cleaning device is stopped in order to prevent dry running of said contamination measurement apparatus.

BRIEF DESCRIPTION OF THE DRAWINGS

The features of the invention are believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1–6 of the drawings in which like numerals refer to like features of the invention.

Figure 1:
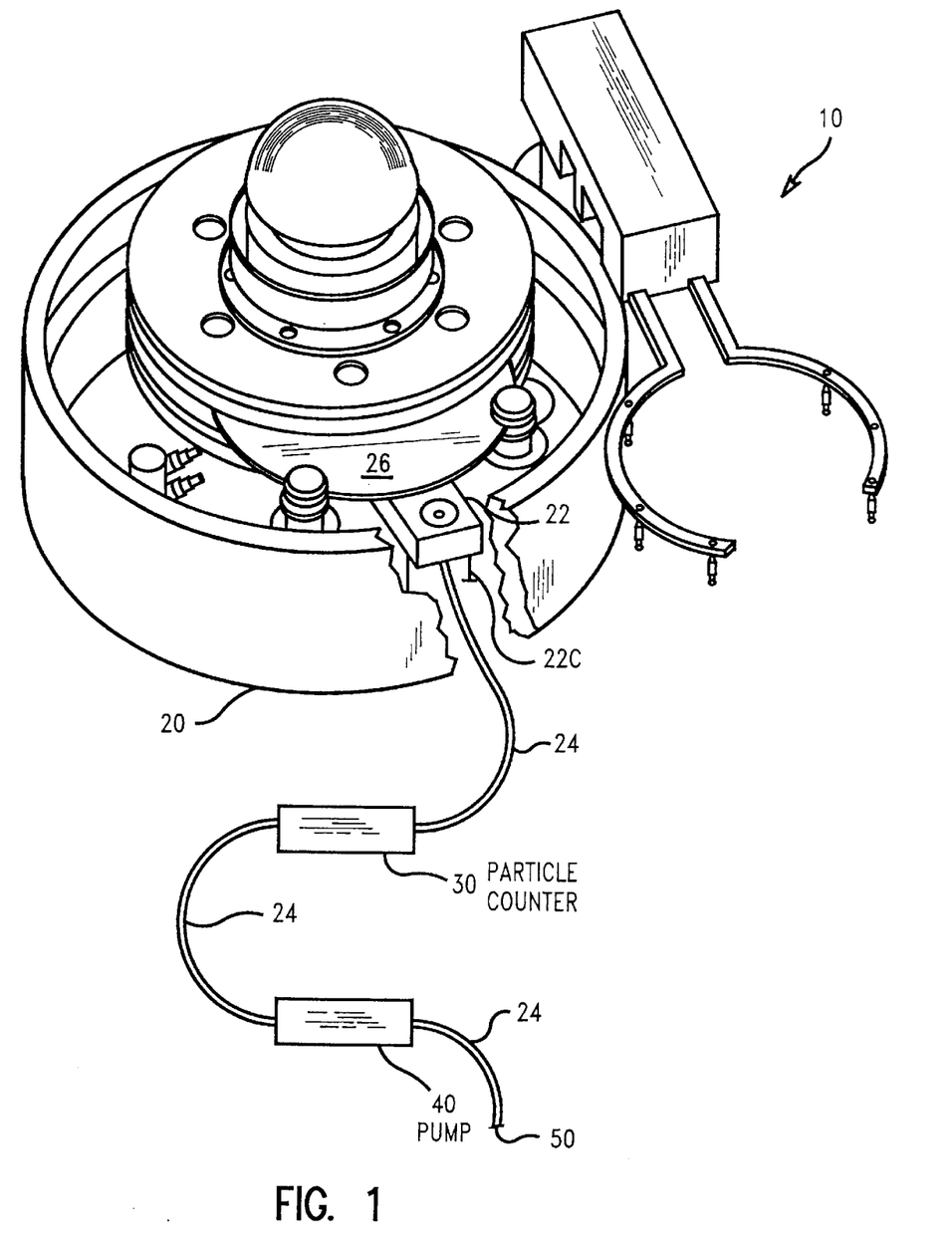
FIG. 1 is a perspective view illustrating a brush assembly for a brush cleaner including the placement of the collection head on the floor of the drain tray for collecting effluent.

The apparatus of the present invention, illustrated in FIG. 1, is a contamination measuring apparatus 10 for measuring effluent contamination comprising a brush cleaning device 20 for cleaning wafers 26; a effluent collection device or collection head 22 and particle counter 30. The collection head 22 is positioned adjacent to the wafer 26 which is placed between brushes 20a, or sponges, in the brush cleaning device 20. The collection head 22 collects effluent 32 which flows off of the wafer 26 which is being cleaned. The particle counter 30 is connected to the collection head by tubing 24 through which effluent 32 flows from the collection head 22 to the particle counter 30.

FIG. 1 illustrates the present invention with the preferred brush cleaning device 20, a Westech 3800 manufactured by IPEC/WESTECH of Phoenix, Ariz. and the collection head preferably positioned at the second brush station. However, other manufacturers' brush cleaning devices may be used with modification of the collection head size and geometry. These modifications can be performed by one of ordinary skill in the art.

Figure 1A:
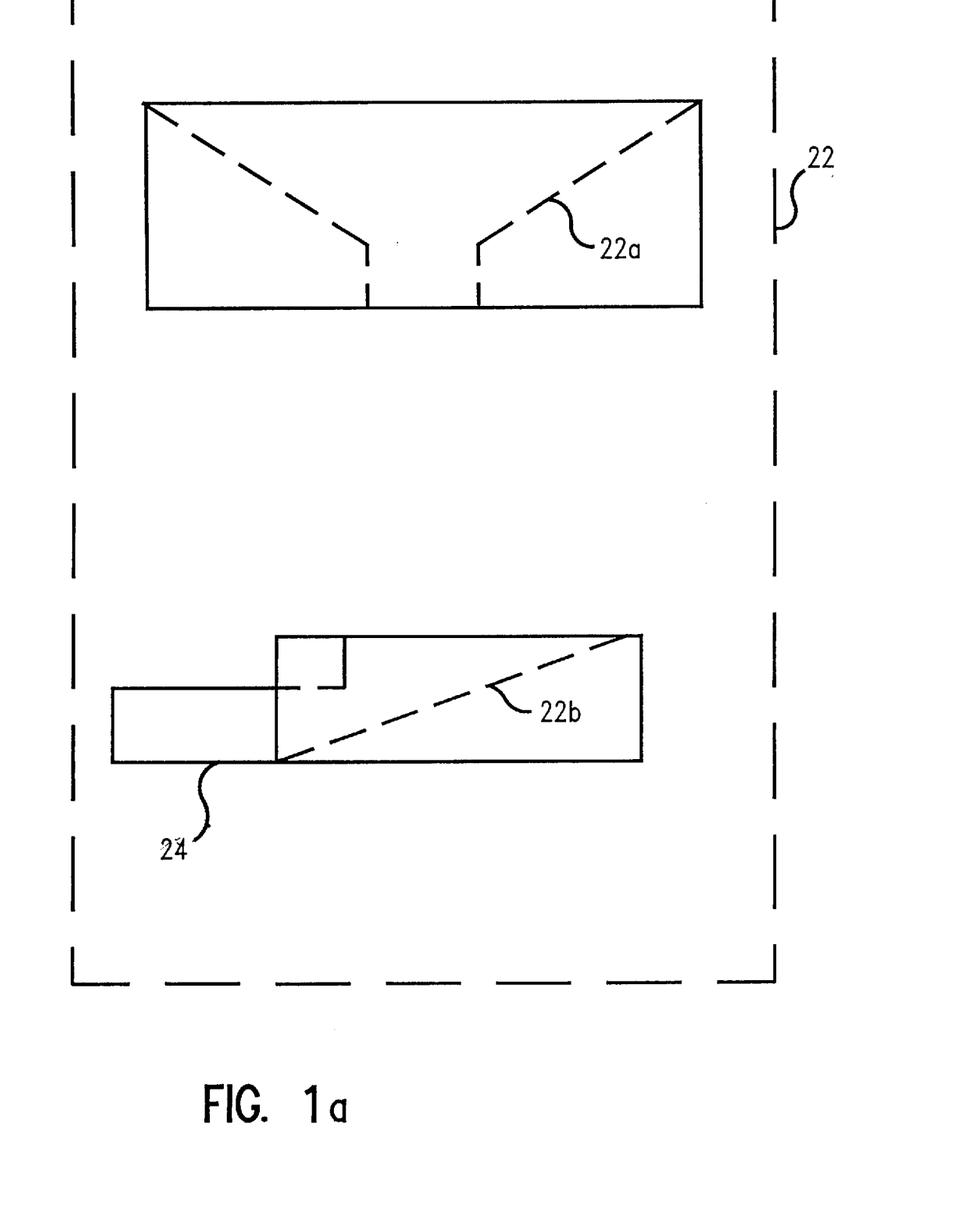
FIG. 1a is a side view of the collection head of FIG. 1 illustrating the configuration of the concentrator and the overflow collector.

FIG. 1a is a side view of the collection head of FIG. 1 and illustrates the configuration of the effluent collector or concentrator 22a and the reservoir or overflow collector 22b. The collection head 22 comprises a concentrator 22a and an overflow collector 22b. The collection head 22 is positioned below and adjacent to the wafer 26 for collecting effluent 32 as it flows off of the wafer 26. The overflow collector 22b is positioned below and adjacent to the collection head 22a for collecting effluent 32 which passes through the concentrator 22a.

The collection head 22 is designed for rapid response to changes in particle counts by minimizing the contained volume in the collection head 22. Additionally, the head is designed to collect liquid which pours over the wafer 26 in an erratic manner. In order to meet these design criteria, the collection head 22 is designed comprising two parts, the concentrator 22a and the collection head 22b. The concentrator, or shallow funnel shape block 22a, concentrates the effluent 32 into a shallow overflow collector, or spoon 22b. This insures that fluid is collected from a wide region, but that the volume collected is kept relatively small, i.e. 5 ml. Due to the small volume in the collection head, the response time to injection of particles is quick. For example, when particles are introduced into the effluent 32 in the overflow collector 22b, the particle count is increased; the particle count subsequently decreases to one-half its original value in 8 seconds as the effluent passes through the collector 22b. Also, the collection head is elevated from the floor of the brush cleaner by elevating apparatus or legs 22c which allow it to be positioned adjacent to the wafer to collect effluent 32 as it pours off the wafer.

Figure 2:
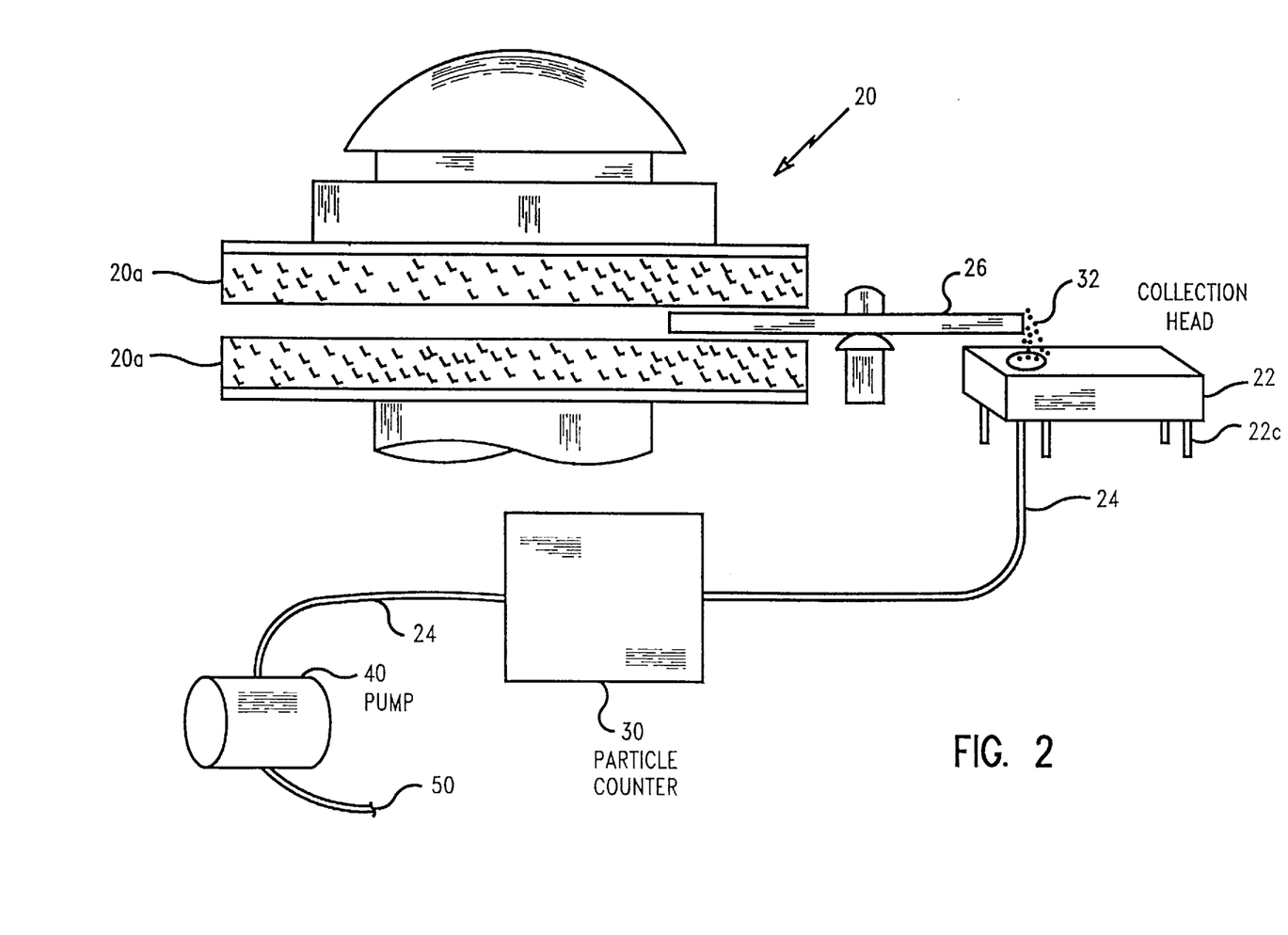
FIG. 2 is a schematic view of the apparatus of the present invention.
Figure 3:
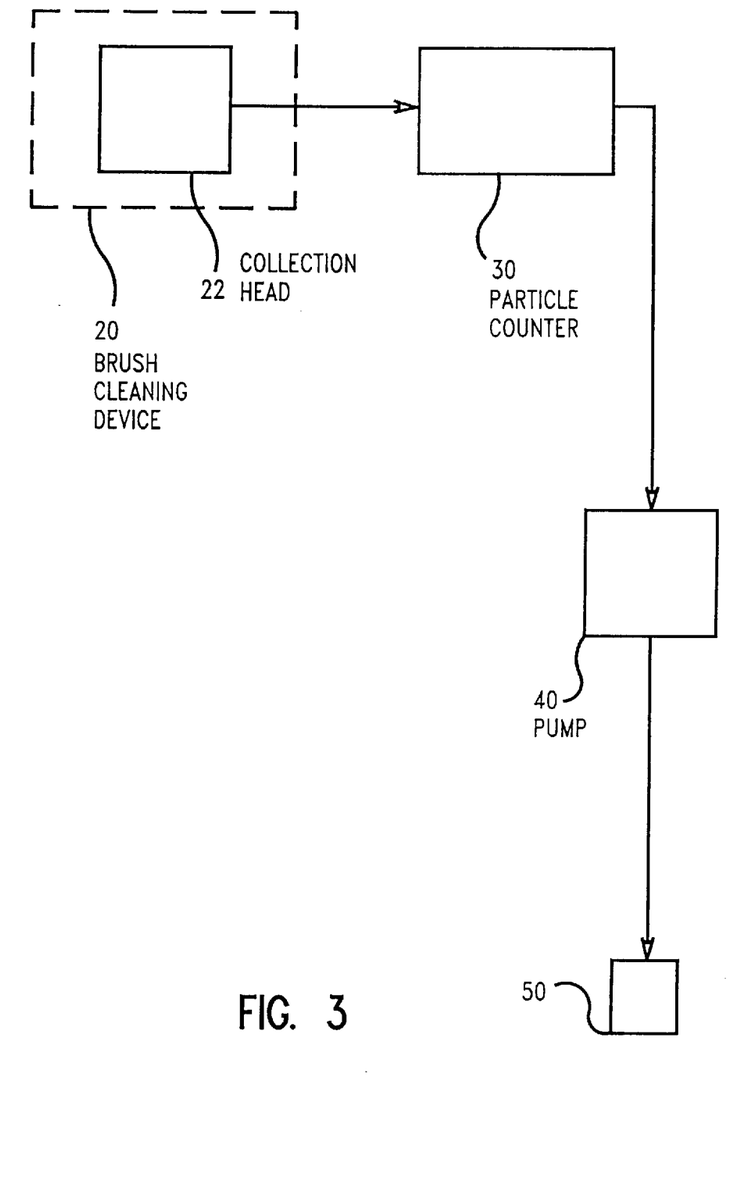
FIG. 3 is a schematic diagram of the effluent flow through the device of the present invention.

FIG. 2 is a schematic view of the contamination measuring apparatus 10 illustrating the flow of effluent 32 off the wafer 26 and into the collection head 22. The particle counter 30 is connected to the collection head 22. Effluent 32 flows from the collection head 22 into the particle counter 30 which counts the number of particles per liter of effluent. Because the flow of liquid to the brushes 20a can be turned off when wafers 26 are not being processed (processing is performed in lots of 25 wafers), a clean trickle flow of liquid is supplied to the concentrator 22a between wafer lots in order to insure that the particle counter 30 does not run dry. Since this trickle flow is very small compared to the effluent 32 coming from the wafer 26, it does not substantially affect the particle counts obtained when the wafer 26 is being cleaned.

FIG. 2 also illustrates the connection of the particle counter 30 to a pump 40 by tubing 24 and the connection of the pump 40 to a drain 50 by tubing 24. Effluent 32 passes from the overflow collector 22b, to the particle counter 30, and then through the pump 40 which provides the suction force to draw liquid through the apparatus 10. Finally the effluent 32 is released to the drain 50. Since the pump is downstream from the particle counter 30, it cannot introduce contamination to the particle counter 30.

The preferred particle counter is the PMS particle counter manufactured by Particle Measurement Systems, Boulder, Colo. It is also preferred that the flow rate and the sensitivity of the particle counter be moderate. For example, a flow rate of 10–30 ml per minute and a sensitivity of 0.1 micron is preferred for 0.035 micron technology line width applications. These setting vary by application. When the flow rate is high, the particle sensitivity of the counter is constrained.

The particle counter 30 counts the particles in 10 second intervals and provides this data via a data port, i.e. an RS232 link, to a recordation device, i.e. a personal computer. A program running on the PC logs the data, graphs the data and can provide network based alarms. The program and recordation of data can be performed by one of ordinary skill in the art. The data can be interpreted and it can be determined whether further action should be taken. For example, the brushes could be reconditioned or replaced, the wafers could be rerun through the process, a test wafer could be run to diagnose corrective action, the brush height could be adjusted or the system ozonated. The proper action would be determined by one of ordinary skill in the art.

Figure 4:
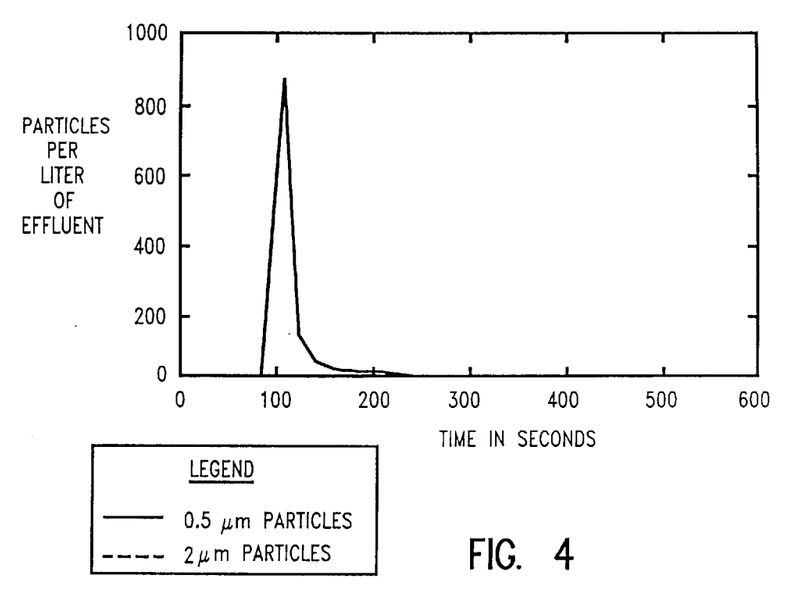
FIG. 4 is a graph illustrating time versus particles per liter of effluent, the peak correlates to the introduction of particles into the effluent.

FIG. 4 is a graph illustrating time versus particles per liter of effluent, wherein particles of $SiO_2$ are deliberately introduced into the effluent at the collection head in order to test the measurement of the particles in the effluent by the particle counter. The peak of the graph correlates to the introduction of particles into the effluent and verifies that the apparatus is functioning as designed.

Figure 5:
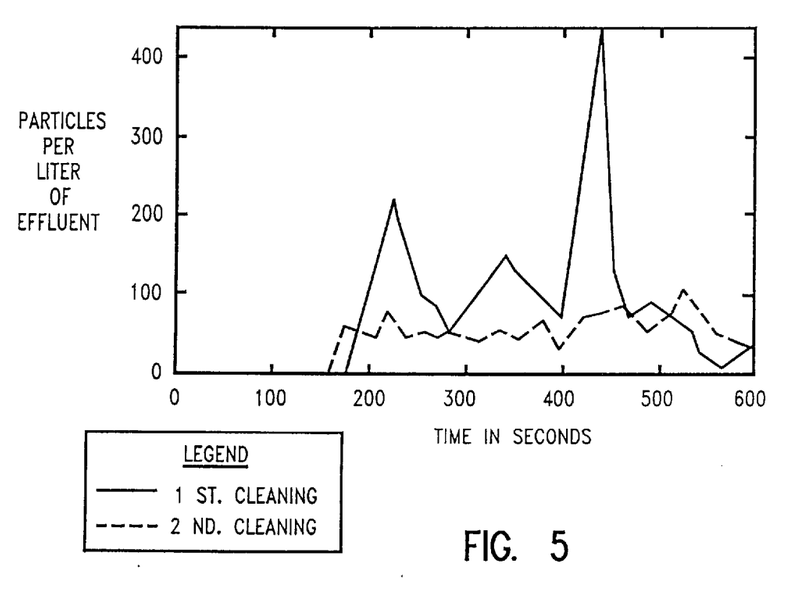
FIG. 5 is a graph illustrating time versus particles per liter of effluent, wherein data is collected from brush cleaning of dirty wafers which were dipped in a slurry of $SiO_2$ and KOH.

FIG. 5 is a graph illustrating time versus particles per liter of effluent, wherein data is collected from brush cleaning of dirty wafers which were dipped in a slurry of $SiO_2$ and KOH. The solid line represents the first cleaning run and the dashed line represents the second cleaning run. A delay in seconds occurs before the brushes scrub the particles from the wafer and the effluent carries the particles away to the particle counter, this is indicated by the later peaks in the graph.

Figure 6:
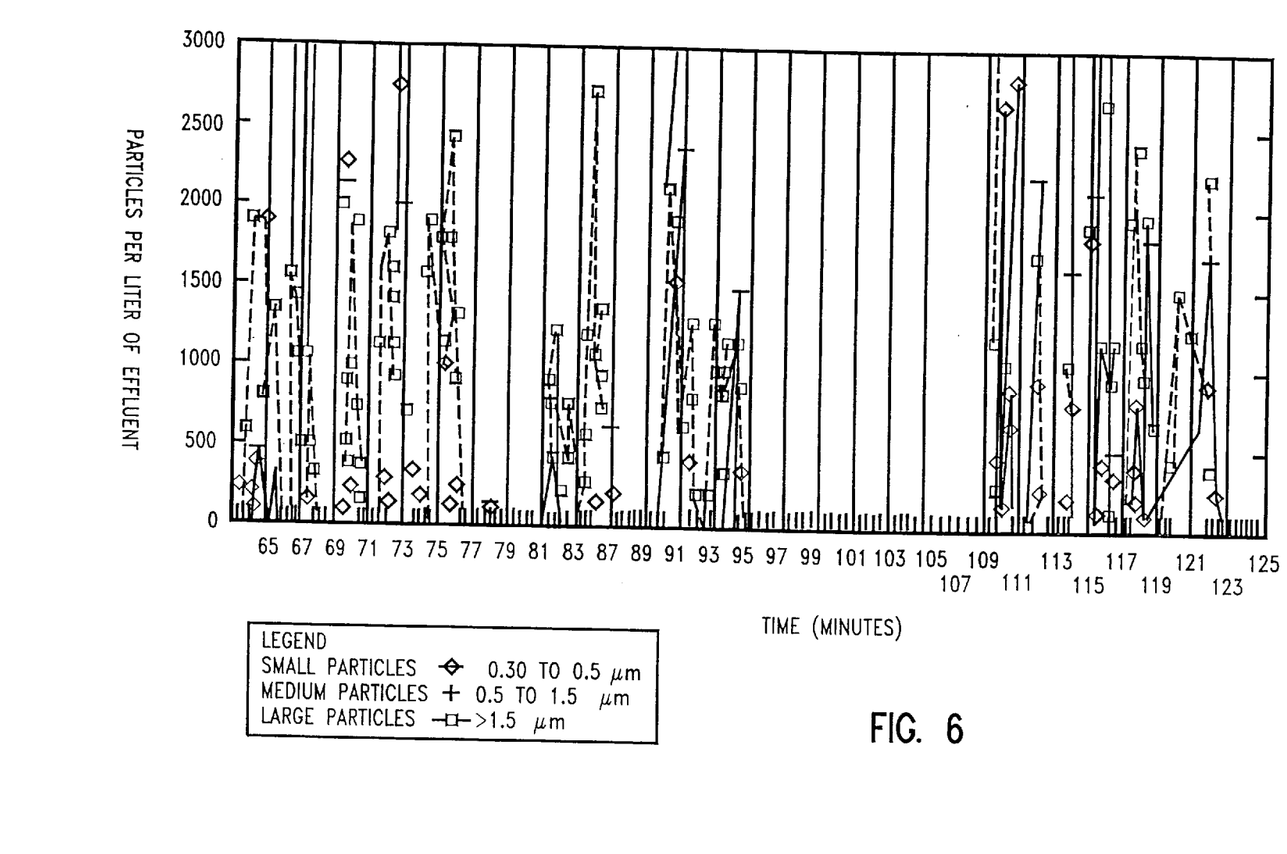
FIG. 6 is a graph illustrating time versus particles per liter of effluent, with each line representing a different range of particle sizes for a series of wafers.

FIG. 6 is a graph illustrating time versus particles per liter of effluent, with each line representing a different range of particle sizes. The graph represents particles per liter of effluent for each individual wafer in the process. This type of graph is used to chose a Statistical Process Control Limit (SPCL) at which point the brushes would be reconditioned or replaced; the SPCL a chosen based upon the size of the brushes and the type of process and can be chosen by one of ordinary skill in the art. For example, for the process of FIG. 6, the upper control limit (ULC) is 2000 particles per liter of effluent and the lower control limit is zero particles per liter of effluent.

Figure 6A:
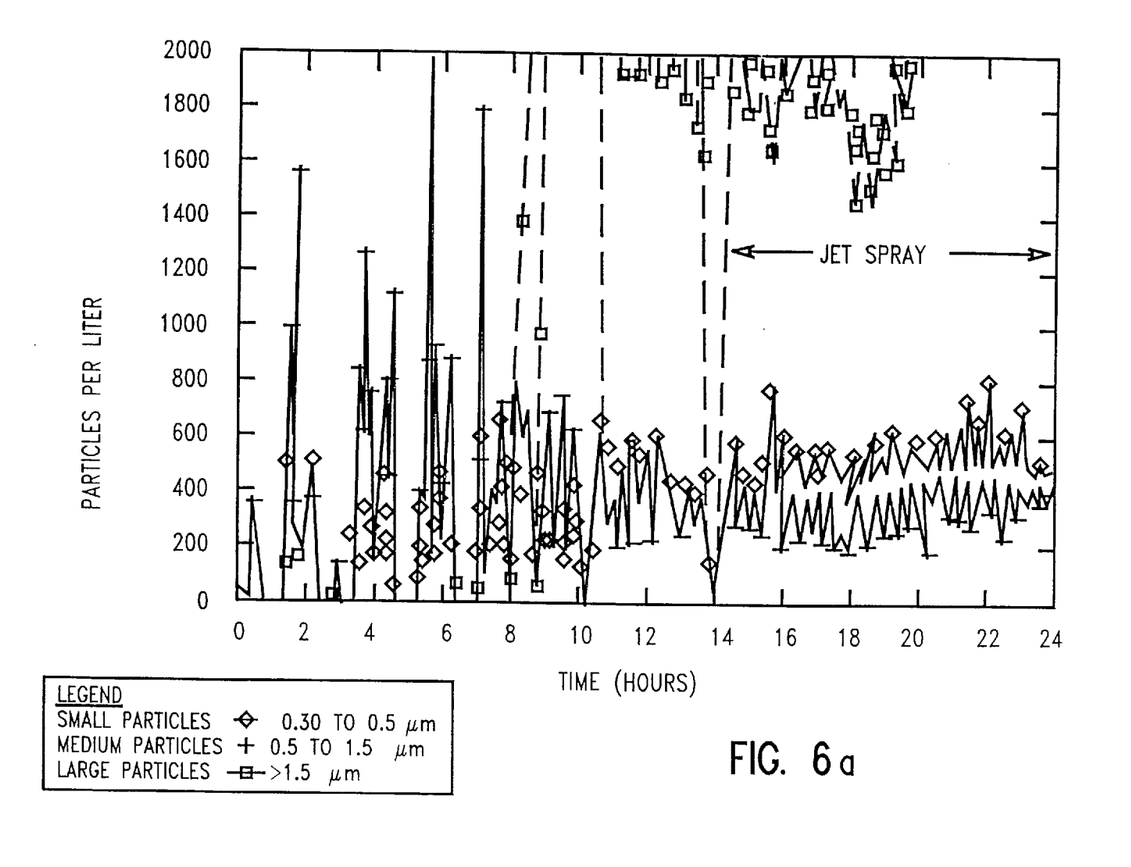
FIG. 6a is a graph illustrating time versus particles per liter of effluent, with each line representing a different range of particle sizes for a series of 25 wafer lots.

FIG. 6a is a graph illustrating time versus particles per liter of effluent, with each line representing a different range of particle sizes. There is clear rise in number of particles during the processing of a lot (25 wafers). Because the jet spray head was dirty, the number of particles per liter of effluent when there are no wafers in the brush cleaner, and the brush cleaner is idling with the jet spray on, are quite high as indicated by the graph during hours 14 through 24.

Data has also indicted that when new or clean brushes are installed, there is a correlation between clean brushes and clean effluent. There was also a correlation between dirty wafers and dirty effluent when average particles counts per liter of effluent were obtained for a lot (25 wafers) and compared to particle counts measured on 4 to 5 wafers from that lot using an INSPEC PPC 8500 scanning laser system which detects topographical defects in pattern anomalies by light scattering. While some scatter was evident, a reasonable correlation existed between foreign matter on the wafer and particles per liter of effluent.

The present invention involves the use of a liquid-born particle counter with a collection head which collects samples of effluent passing over the wafer during CMP brush cleaning. There is a correlation between the contamination of the effluent and the contamination of the brushes. The novel approach utilizes real-time monitoring in order to prevent unnecessary tool down time. Furthermore, since it measures the effluent of CMP brush cleaning, if the deionized water (DI) system is contaminated, for example, by high bacteria counts or solid content, the problem can be detected by the present invention. Thereby, potential wafers contamination with DI water contaminants is avoided. The invention can also be used to determine if the brush loading has become too great and the brushes need to be replaced. The device of the present invention may also be used as a real-time continuous monitor which would replace daily foreign matter monitoring which is time consuming because it requires stopping the brushes and therefore, stopping the process.

This invention demonstrates the effectiveness of monitoring the brush cleaner effluent for particulate contamination in order to predicting wafer cleanliness. Furthermore, it can be used to indicate when the brushes are being changed too often, which is very costly in because of the loss of production time during tool maintenance and. because of the high cost of brushes. It provides a method of real-time monitoring of brush cleaners at reasonable cost, thus providing earlier detection of tool failures and improved maintenance schedules.

Utilizing the approach of the present invention, the brush-clean effectiveness can be predicted, thereby reducing the above cited problems.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of measuring brush contamination in a cleaning device for cleaning wafers comprising the steps of:
   (a) providing a contamination measurement apparatus further comprising:
     (i) a reservoir;
     (ii) an effluent collector having a first opening for receiving effluent flowing off of an area of the wafer which is adjacent to the effluent collector, said collector having a second opening smaller than said first opening for discharging effluent into said reservoir, said reservoir for holding a volume of effluent collected by said effluent collector, said reservoir positioned adjacent to said effluent: collector second opening; and
     (iii) a particle counter connected to said reservoir for measuring contamination of the effluent;
   (b) passing the effluent from said effluent collector to said particle counter for measurement of contamination of the effluent;
   (c) recording the data collected by said particle counter in an electronic recordation means;
   (d) comparing the data collected by said particle counter to predetermined values stored in said electronic recordation means;
   (e) stopping said brush cleaning device when the data correlates to the predetermined values which indicate the cleanliness of brushes in said brush cleaning device; and
   (f) providing a trickle flow of liquid to said effluent collector while said brush cleaning device is stopped in order to prevent dry running of said contamination measurement apparatus.

2. The method as claimed in claim 1 further comprising the steps of:
   (g) replacing the brushes.

3. The method as claimed in claim 2 further comprising the steps of:
   (h) resuming the wafer cleaning process; and (i) repeating steps (b)–(f) during the cleaning process.

4. The method as claimed in claim 1 further comprising the steps of:

(g) reconditioning the brushes.

5. The method as claimed in claim 4 further comprising the steps of:

(h) resuming the wafer cleaning process; and (i) repeating steps (b)–(f) during the cleaning process.

6. The method as claimed in claim 1 further comprising in step (a) providing a contamination measurement apparatus further comprising:

(iv) a pump connected to said particle counter for facilitating removal of the effluent; and (v) a drain connected to said pump for draining the effluent from said measuring apparatus.

7. The method as claimed in claim 6 further comprising:

(l) pumping the effluent from said particle counter at a flow rate coordinated with the flow rate of said particle counter.

* * * * *